United States Patent [19]

Maschler et al.

[11] Patent Number: 5,362,915
[45] Date of Patent: Nov. 8, 1994

[54] PHENYL-SUBSTITUTED CYCLOALKENYL COMPOUNDS USEFUL AS PDE IV INHIBITORS

[75] Inventors: Harald Maschler, Nordstemmen, Germany; Siegfried B. Christensen, IV, King of Prussia, Pa.

[73] Assignees: SmithKline Beecham Pharma GmbH, Munich, Germany; SmithKline Beecham Corporation, King of Prussia, Pa.

[21] Appl. No.: 934,546

[22] PCT Filed: Apr. 2, 1991

[86] PCT No.: PCT/EP91/00637

§ 371 Date: Oct. 2, 1992

§ 102(e) Date: Oct. 2, 1992

[87] PCT Pub. No.: WO91/15451

PCT Pub. Date: Oct. 17, 1991

[30] Foreign Application Priority Data

Apr. 5, 1990 [GB] United Kingdom ............... 9007762

[51] Int. Cl.$^5$ ............... C07C 43/205; A61K 31/075
[52] U.S. Cl. .......................... 568/20; 568/42; 568/49; 568/52; 568/329; 568/330; 568/644
[58] Field of Search .............. 568/644, 20, 42, 49, 568/52, 329, 330; 514/719, 683, 684, 706, 712

[56] References Cited

U.S. PATENT DOCUMENTS 4,831,059  5/1989  Johnson et al.

FOREIGN PATENT DOCUMENTS 140454  3/1990  Germany.

OTHER PUBLICATIONS

Chem. Abs. vol. 110; No. 1, 1989 Jan. 2, B. Deb et al., p. 705, Abstract No. 7698g.
Chem. Abs. vol. 85, No. 25, 1976 Dec. 20, D. A. Pisanenko et al., p. 529, Abstract No. 192459f.
Chem. Abs. vol. 100; No. 1, 1984 Jan. 2, Katsumi Itoh et al., p. 505, Abstract No. 5901n.

Deb, B. et al.; Tet. Lett., vol. 29(17), pp. 2111–2114 (1988).
Psotta, K. et al.; Tetrahedron, vol. 35, pp. 255–257 (1979).
Pisanenko, D. A. et al.; Tezisy Dokl.-Simp. Khim. Tekhnol. Geterotsikl. Soedin. Goryuch. Iskop., 2nd, pp. 200–201 (1973).

Primary Examiner—Johann Richter
Assistant Examiner—Michael B. Hydorn
Attorney, Agent, or Firm—James M. Kanagy; Stuart R. Suter; Edward T. Lentz

[57] ABSTRACT

A compound of formula (I) or a pharmaceutically acceptable salt thereof:

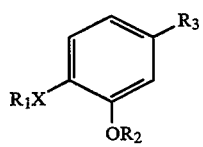

wherein:
$R_1$ is $-CH_3$ or $-CH_2CH_3$ unsubstituted or substituted by 1 to 3 fluorines;
X is O or $S(O)_s$ where s = 0 to 2;
$R_2$ is $C_4$–$C_6$ cyclic alkyl, optionally substituted by one to three methyl groups or one ethyl group; $-CH_2$-cyclopentyl, $-CH_2$-cyclopropyl, 3-tetrahydrofuranyl, $C_{1-7}$ alkyl, $CH_3$ or $CH_2CH_3$ substituted by one to three fluorines;
$-(CH_2)_nCOO(CH_2)_gCH_3$, or $(CH_2)_nO(CH_2)_gCH_3$, wherein n is 2 to 4 and g is 0 to 2;
$R_3$ represents a moiety of formula (a);

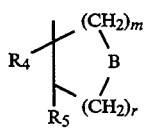

wherein $R_4$ and $R_5$ each represent hydrogen or $R_4$ and $R_5$ together represent a bond;
B represents $>C=O$, $>C=S$ or $>CH-R_6$ wherein (Abstract continued on next page.)

$R_6$ represents H, OH, $C_{1-6}$ alkoxy or $C_{1-6}$ thioalkoxy; and m and r each independently represents zero or an integer in the range of 1 to 4 wherein $m+r$ represents an integer in the range of from 2 to 4; with the proviso that when $R_1$ is methyl, X is oxygen, $R_2$ is methyl or cyclopenyl, $R_3$ does not represent cyclopent-1,2,-ene-3-one.

8 Claims, No Drawings

PHENYL-SUBSTITUTED CYCLOALKENYL COMPOUNDS USEFUL AS PDE IV INHIBITORS

The present invention relates to novel compounds having pharmacological activity, to a process for the preparation of such compounds, to pharmaceutical compositions containing such compounds and to the use of such compounds and compositions in medicine.

A French thesis by Michel Marivet entitled 'Contribution A L'Etude, Des Inhibiteurs De Phosphodiesterases' which was submitted on 23rd January 1987 to the University of Louis Pasteur in Strasbourg describes the following compounds

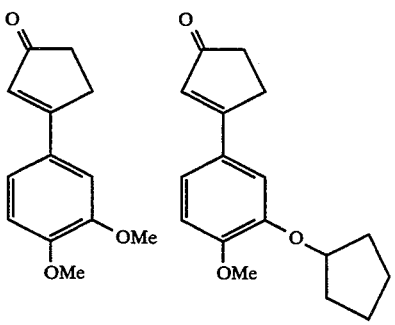

It has now been discovered that certain novel compounds have potent and selective phosphodiesterase (IV) inhibition activity and elevate cyclic AMP levels. These compounds also inhibit TNF production.

Accordingly, the present invention provides a compound of formula (I):

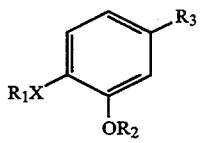

wherein:

$R_1$ is —$CH_3$ or —$CH_2CH_3$ unsubstituted or substituted by 1 to 3 fluorines;

X is O or $S(O)_s$ where s=0 to 2;

$R_2$ is $C_4$–$C_6$ cyclic alkyl, optionally substituted by one to three methyl groups or one ethyl group; —$CH_2$-cyclopentyl, —$CH_2$-cyclopropyl, 3-tetrahydrofuranyl, $C_{1-7}$ alkyl, $CH_3$ or $CH_2CH_3$ substituted by one to three fluorines;

—$(CH_2)_nCOO(CH_2)_gCH_3$, or $(CH_2)_nO(CH_2)_gCH_3$, wherein n is 2 to 4 and g is 0 to 2;

$R_3$ represents a moiety of formula (a);

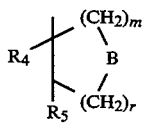

wherein $R_4$ and $R_5$ each represent hydrogen or $R_4$ and $R_5$ together represent a bond;

B represents >C=O, >C=S or >CH—$R_6$ wherein $R_6$ represents H, OH, $C_{1-6}$ alkoxy or $C_{1-6}$ thioalkoxy; and m and r each independently represents zero or an integer in the range of 1 to 4 wherein m+r represents an integer in the range of from 2 to 4; with the proviso that when $R_1$ is methyl, X is oxygen and, $R_2$ is methyl or cyclopentyl, $R_3$ does not represent cyclopent-1,2-ene-3-one.

Suitably, $R_1$ represents methyl.

Suitably, $R_2$ represents unsubstituted C4–C6 cycloalkyl.

Favourably, $R_2$ is cyclopentyl or methyl and X is oxygen.

Suitably $R_3$ is selected from the following structures:

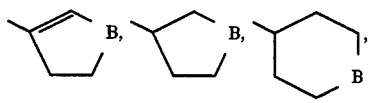

b)   c)   d)

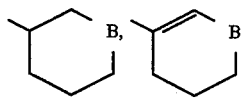

e)   f)

wherein B is C=O, $CH_2$, —$CH_2OH$ or $CH_2OCH_3$.

Preferably $R_3$ is of formula b) or c) and B is carbonyl, $CH_2OH$ or $CH_2OCH_3$.

Suitable salts are pharmaceutically acceptable salts.

It should be appreciated that some compounds of formula (I) may exist as geometric and/or stereo isomers. The present invention includes single geometric and/or stereo isomers and any mixtures thereof.

These compounds by virtue of their PDE IV activity are useful in the treatment of a variety of allergic and inflammatory diseases including: asthma, chronic bronchitis, atopic dermatitis, urticaria, allergic rhinitis, allergic conjunctivitis, vernal conjunctivitis, eosinophillic granuloma, psoriasis, rheumatoic arthritis, septic shock, ulcerative colitis, Crohn's disease, reperfusion injury of the myocardium and brain, chronic glomerulonephritis, endotoxic shock and adult respiratory distress syndrome. In addition, PDE IV inhibitors are useful in the treatment of diabetes insipidus, (Kidney Int. 37: 362, 1990; Kidney Int. 35: 494, 1989).

These compounds also have a protective effect against the consequences of cerebral metabolic inhibition the said compounds improve data acquisition or retrieval following transient forebrain ischaemia and are therefore useful in the treatment of cerebral vascular and neuronal degenerative disorders associated with learning, memory and cognitive dysfunctions including cerebral senility, multi-infarct dementia, senile dementia of the Alzheimer type, age associated memory impairment and certain disorders associated with Parkinson's disease.

These compounds are also indicated to have neuroprotectant activity. They are therefore useful in the prophylaxis of disorders associated with neuronal degeneration resulting from ischaemic events, including cerebral ischaemia due to cardiac arrest, stroke and also after cerebral ischaemic events such as those resulting from surgery and/or during childbirth. In addition treatment with the compound is indicated to be of benefit for the treatment of functional disorders resulting from disturbed brain function following ischaemia.

The compounds are also active in increasing the oxygen tension in ischaemic skeletal muscle. This property results in an increase in the nutritional blood flow through ischaemic skeletal muscle which in turn indicates that the compounds of the invention are of potential use as agents for the treatment of peripheral vascular disease such as intermittent claudication.

These compounds are also of potential use in the treatment of proliferative skin disease in human or non-human mammals.

When used herein the expression 'proliferative skin diseases' means benign and malignant proliferative skin diseases which are characterized by accelerated cell division in the epidermis, dermis or appendages thereto, associated with incomplete tissue differentiation. Such diseases include: psoriasis, atopic dermatitis, non-specific dermatitis, primary irritant contact dermatitis, allergic contact dermatitis, basal and squamous cell carcinomas of the skin, lamellar ichthyosis, epidermolytic hyperkeratosis, premalignant sun induced keratosis, non-malignant keratosis, acne, and seborrheic dermatitis in humans and atopic dermatitis and mange in domesticated animals.

The compounds of this invention also inhibit production of Tumor Necrosis Factor (TNF), a serum glycoprotein. Excessive or unregulated TNF production is implicated in mediating or exacerbating a number of diseases including rheumatoid arthritis, rheumatoid spondylitis, osteoarthritis, gouty arthritis and other arthritic conditions; sepsis, septic shock, endotoxic shock, gram negative sepsis, toxic shock syndrome, adult respiratory distress syndrome, cerebreal malaria, chronic pulmonary inflammatory disease, bone resorption diseases, silicosis, pulmonary sarcoisosis, reperfusion injury, grafts vs. host reaction, allograft rejections fever and myalgias due to infection, such as influenza, cachexia secondary to infection or malignancy, cachexia secondary to acute immune deficiency syndrome (AIDS), AIDS (ARC/AIDS related complex) keloid formation, scar tissue formation, Crohn's disease, ulcerative coliris, or pyresis.

TNF has been implicated in various roles with the human acquired immune deficiency syndrome (AIDS). AIDS results from the infection of T lymphocytes with Human Immunodeficiency Virus (HIV). It has now been discovered that monokines, specifically TNF, are implicated in the infection of T lymphocytes with HIV by playing a role in maintaining T lymphocyte activation. Furthermore, once an activated T lymphocyte is infected with HIV, the T lymphocyte must continue to be maintained in an activated state to permit HIV gene expression and/or HIV replication. It has also been discovered that monokines, specifically TNF, are implicated in activated T-cell mediated HIV protein expression and/or virus replication by playing a role, in maintaining T lymphocyte activation. Therefore, interference with monokine activity such as by inhibition of monokine production, notably TNF, in an HIV-infected individual aids in limiting the maintenance of T cell activation thereby reducing the progression of HIV infectivity to previously uninfected cells which results in a slowing or elimination of the progression of immune dysfunction caused by HIV infection. Monocytes, macrophages, and related cells, such as kupffer and glial cells, have also been implicated in maintenance of the HIV infection. These cells, like T-cells, are targets for viral replication and the level of viral replication is dependent upon the activation state of the cells. [See Rosenberg et al., The Immunopathogenesis of HIV infection, *Advances in Immunology*, Vol. 57, (1989)].

Monokines, such as TNF, have been shown to activate HIV replication in monocytes and/or macrophages [See Poli, et al., *Proc. Natl. Acad. Sci.*, 87:782-784 (1990)], therefore, inhibition of monokine production or activity aids in limiting HIV progression as stated above for T-cells.

It has now been discovered that monokines are implicated in certain disease associated problems such as cachexia and muscle degeneration. Therefore, interference with monokine activity, such as by inhibition of TNF production, in an HIV-infected individual aids in enhancing the quality of life of HIV-infected patients by reducing the severity of monokine-medicated disease associated problems such as cachexia and muscle degeneration.

By the term "cytokine" as used herein is meant any secreted polypeptide that affects the functions of other cells, and is a molecule which modulates interactions between cells in the immune or inflammatory response. A cytokine includes, but is not limited to monokines and lymphokines regardless of which cells produce them. For instance, a monokine is generally referred to as being produced and secreted by a mononuclear cell, such as a macrophage and/or monocyte but many other cells produce monokines, such as nutural killer cells, fibroblasts, basophils, neutraphils, endothelial cells, brain astrocytes, bone marrow stromal cells; epideral keratinocytes, and $\beta$-lymphocytes. Lymphokines are generally referred to as being produced by lymphocyte cells. Examples of cytokines for the present invention include, but are not limited to, Interleukin-1 (IL-1), Interleukin-6 (IL-6), Tumor Necrosis Factor-alpha (TNF$\alpha$) and Tumor Necrosis Factor beta (TNF$\beta$).

By the term "inhibiting the production of TNF" is meant a) a decrease of excessive in vivo TNF levels in a human to normal levels or below normal levels by inhibition of the in vivo release of TNF by all cells, including but not limited to monocytes or macrophages;

b) a down regulation, at the translational or transcription level, of excessive in vivo TNF levels in a human to normal levels or below normal levels; or c) a down regulation, by inhibition of the direct synthesis of TNF as a postranslational event.

By the term "TNF mediated disease or disease states" is meant any and all disease states in which TNF plays a role, either by production of TNF itself, or by TNF causing another cytokine to be released, such as but not limited to IL-1, or IL-6. A disease state in which IL-1, for instance is a major component, and whose production or action, is exacerbated or secreted in resoponse to TNF, would therefore of considered a disease state medicated by TNF.

The discovery of a class of compounds which inhibit the production of TNF will provide a therapeutic approach for the disease in which excessive, or unregulated TNF production is implicated.

The compounds of this invention are, therefore, useful in treating, prophylactically or therapeutically, disease states in humans which are exacerbated or caused by excessive or unregulated TNF production.

The compounds of formula (I) are preferably in pharmaceutically acceptable form. By pharmaceutically acceptable form is meant, inter alia, of a pharmaceutically acceptable level of purity excluding normal pharmaceutical additives such as diluents and carriers, and including no material considered toxic at normal dosage levels. A pharmaceutically acceptable level of purity will generally be at least 50% excluding normal pharmaceutical additives, preferably 75%, more preferably 90%, and still more preferably 95%.

The invention further provides a process for the preparation of a compound of formula (I), which process comprises reacting a compound of formula (II):

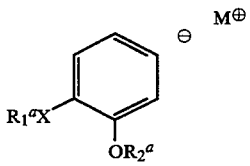

wherein $R_1^a$ represents $R_1$, as defined in relation to formula (I), or a group convertible to $R_1$ and $R_2^a$ represents $R_2$, as defined in relation to formula (I), or a group convertible thereto and $M^+$ is a counter-ion, with a compound of formula (III):

$$R_3—X' \quad (III)$$

wherein $R_3$ is as defined above in relation to formula (I), and X' is a leaving group; and thereafter, if required carrying out one or more of the following optional steps:

(i) converting any group $R_1^a$ to $R_1$ and/or $R_2^a$ to $R_2$;
(ii) interconverting $R_3$;
(iii) converting a compound of formula (I) into a pharmaceutically acceptable salt thereof, or a solvate thereof.

A suitable counter-ion $M^+$ is a lithium ion.

A suitable leaving group X' is an alkoxy group such as an ethoxy group or an isopropoxy group.

The reaction between a compound of formula (II) and a compound of formula (III) may be carried out under any suitable reaction conditions providing a convenient rate of formation of the desired product, for example in any suitable inert solvent, such as n-hexane or THF at any convenient temperature, generally at ambient temperature, and preferably under an inert atmosphere.

Interconversions of $R_3$ are carried out by conventional procedures in the art of organic chemistry. For example:

a) an $R_3$ 1-cyclohex-1,2-ene-3-one group may be converted to a 1-cyclohexane group by catalytic hydrogenation using a suitable catalyst such as palladium on carbon in a suitable solvent such as absolute ethanol under pressure, for example 1 to 5 bar, preferably 2 to 3 bar pressure.

b) an $R_3$ 3-cyclopent-2-ene-1-one group may be converted to a an 3-cyclopentan-1-one group and cyclopentan-1-ol group (which are separated by conventional means) by catalytic hydrogenation using a suitable catalyst such as palladium on carbon in a suitble solvent such as methanol optionally in a presence of a base such as potassium hydroxide c) an $R_3$ 3-cyclopent-2-en-1-one group may be converted to a 3-cyclopent-2-en-1-ol group by reduction using a suitable reducing agent such as diisobutylaluminum hydride in an inert solvent such as benzene at a reduced temperature.

d) an $R_3$ 3-cyclopent-2-en-1-ol group may be converted to a 3-(1-methoxy)cyclopent-2-ene group by conventional methylation for example using iodomethane in the presence of a base.

e) an $R_3$ cis-3-cyclopentan-1-ol group may be converted to a trans configuration using diethylazodicarboxylate, triphenylphosphine and glacial acetic acid in an inert solvent such as THF.

f) an $R_3$ 3-cyclopentan-1-ol group may be converted to a 3-(methoxy)cyclopentane group by conventional methylation, for example using dimethyl sulphate, tetrabutylammonium bromide in the presence of a suitable base such as sodium hydroxide.

A compound of formula (II) may be prepared by reacting a compound of formula (IV):

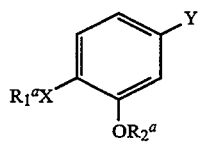

wherein $R_1^a$ and $R_2^a$ are as defined in relation to formula (II) and Y represents a leaving group, with a source of metal ions $M^+$.

A suitable source of metal ions $M^+$ is an alkyl metal compound especially an alkyllithium compound such as butyl lithium.

A suitable leaving group Y is a halogen atom, such as bromine.

The reaction of the compound of formula (IV) and the source of metal ions may be carried out under any convenient reaction conditions, for example in an inert solvent such as n-hexane or THF, at ambient temperature and preferably under an inert atmosphere.

In a preferred aspect of the process for the preparation of a compound of formula (I), the compound of formula (II) is prepared in-situ from the compound of formula (IV) and the source of metal ions, and thereafter reacted with the compound of formula (III).

The compound of formula (IV) may be prepared by reacting a compound of formula (V):

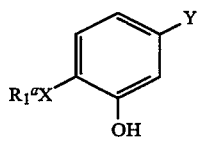

wherein $R_1^a$ and Y are as defined in relation to formula (IV), with a compound of formula (VI):

$$R_3—Z \quad (VI)$$

wherein $R_3$ is as defined in relation to formula (II) and Z is a leaving group, such as a halogen atom and preferably a bromine atom.

The reaction between the compounds of formula (V) and (VI) may be carried out under any suitable conditions, for example in aqueous or non-aqueous conditions, suitably at an elevated temperature, such as the reflux temperature of the solvent, and preferably in the presence of a base, such as sodium hydroxide or potassium carbonate.

Preferably, $R_1^a$ $R_1$. Preferably, is $R_2^a$ is $R_2$.

The compounds of formulae (III), (V) and (VI) are known, commercially available compounds or they may be prepared according to methods used to prepare such compounds.

As stated above the compounds of the invention are indicated to have useful pharmaceutical activity:

Accordingly, the present invention provides a pharmaceutical composition comprising a non-toxic, pharmaceutically acceptable amount of a compound of formula (I) and a pharmaceutically acceptable carrier.

The active compound may be formulated for administration by any suitable route, the preferred route depending upon the disorder for which treatment is required, and is preferably in unit dosage form or in a form that a human patient may administer to himself in a single dosage. Advantageously, the composition is suitable for oral, rectal, topical, parenteral, intravenous or intramuscular administration or through the respiratory tract. Preparations may be designed to give slow release of the active ingredient.

The compositions of the invention may be in the form of tablets, capsules, sachets, vials, powders, granules, lozenges, suppositories, reconstitutable powders, or liquid preparations such as oral or sterile parenteral solutions or suspensions. Topical formulations are also envisaged where appropriate.

In order to obtain consistency of administration it is preferred that a composition of the invention is in the form of a unit dose.

Unit dose presentation forms for oral administration may be tablets and capsules and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulphate.

The solid oral compositions may be prepared by conventional methods of blending, filling, tabletting or the like. Repeated blending operations may be used to distribute the active agent throughout those compositions employing large quantities of fillers.

Such operations are of course conventional in the art. The tablets may be coated according to methods well known in normal pharmaceutical practice, in particular with an enteric coating.

Oral liquid preparations may be in the form of, for example, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia; non-aqueous vehicles (which may include edible oils), for example almond oil, fractionated coconut oil, oily esters such as esters of glycerine, propylene glycol, or ethyl alcohol; preservatives, for example methyl or propyl p-hydroxybenzoate or sorbic acid; and if desired conventional flavouring or colouring agents.

Compositions may also suitably be presented for administration to the respiratory tract as a snuff or an aerosol or solution for a nebulizer, or as a microfine powder for insufflation, alone or in combination with an inert carrier such as lactose. In such a case the particles of active compound suitably have diameters of less than 50 microns, such as from 0.1 to 50 microns, preferably less than 10 microns, for example from 1 to 10 microns, 1 to 5 microns or from 2 to 5 microns. Where appropriate, small amounts of other anti-asthmatics and bronchodilators, for example sympathomimetic amines such as isoprenaline, isoetharine, salbutamol, phenylephrine and ephedrine; xanthine derivatives such as theophylline and aminophylline and corticosteroids such as prednisolone and adrenal stimulants such as ACTH may be included.

For parenteral administration, fluid unit dosage forms are prepared utilizing the compound and a sterile vehicle, and, depending on the concentration used, can be either suspended or dissolved in the vehicle. In preparing solutions the compound can be dissolved in water for injection and filter sterilized before filling into a suitable vial or ampoule and sealing.

Advantageously, adjuvants such as a local anaesthetic, a preservative and buffering agents can be dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compositions may contain from 0.1% to 99% by weight, preferably from 10-60% by weight, of the active material, depending on the method of administration.

Compounds of formula (I) may also be administered as a topical formulation in combination with conventional topical excipients.

Topical formulations may be presented as, for instance, ointments, creams or lotions, impregnated dressings, gels, gel sticks, spray and aerosols, and may contain appropriate conventional additives such as preservatives, solvents to assist drug penetration and emollients in ointments and creams. The formulations may contain compatible conventional carriers, such as cream or ointment bases and ethanol or oleyl alcohol for lotions.

Suitable cream, lotion, gel, stick, ointment, spray or aerosol formulations that may be used for compounds of formula (I) are conventional formulations well known in the art, for example, as described in standard text books of pharmaceutics and cosmetics, such as Harry's Cosmeticology published by Leonard Hill Books, Remington's Pharmaceutical Sciences, and the British and US Pharmacopoeias.

Suitably, the compound of formula (I) will comprise from about 0.5 to 20% by weight of the formulation, favourably from about 1 to 10%, for example 2 to 5%.

This invention constitutes a method for inhibiting phosphodiesterase IV in an animal, including humans, which comprises administering to an animal in need thereof an effective amount of a compound of formula (I).

The present invention also provides a method for the treatment of reversible airways obstruction and asthma in mammals including humans which comprises administering to the mammal in need of such treatment an effective amount of a compound of formula (I).

The invention further provides a method of treatment in mammals, including humans, of cerebrovascular disorders and/or neuronal degenerative disorders associated with learning, memory and cognitive dysfunctions, including cerebral senility, multi-infarct dementia and senile dementia of the Alzheimer type, which comprises administering to the sufferer an effective, non-toxic amount of a compound of formula (I).

The invention further provides a method of treatment of allergic and inflammatory diseases which comprises administering to a subject in need thereof an effective amount of a compound of formula (I).

The invention further provides a method for the treatment of peripheral vascular disease in mammals including humans, which comprises administering to the sufferer an effective, non-toxic amount of a compound of formula (I).

In yet a further aspect, the present invention provides a method for the prophylaxis of disorders associated with neuronal degeneration, following an ischaemic event in mammals, especially humans, which method comprises the administration to the sufferer of an effective, non-toxic, amount of the compound of formula (I).

In a further distinct but related aspect, the disorders resulting from the ischaemic event includes functional disorders resulting from disturbed brain function following the ischaemic event, such as speech and locomotive disorders, sensory disorders, the loss of social skills and other such behavioural disorders associated with the post-ischaemic period.

In another aspect, the present invention provides a method for the treatment of proliferative skin disease in mammals including humans which comprises administering to the mammal in need of such treatment an effective amount of a compound of formula (I).

In another aspect, the present invention prodvides a method for the inhibition of the production of tumor necrosis factor (TNF) in a mammal in need thereof including humans which comprises administering to the mammal in need of such treatment an effective amount of a compound of formula (I) or (I)'.

The present invention also provides a method of preventing a TNF mediated disease state in a mammal in need thereof, including human, by prophylactically administering an effective amount of a compound of formula (I) or (I)':

It should be appreciated that compounds of formula (I)' are 1-(3,4-Dimethoxyphenyl)-cyclopent-1,2-ene-3-one and 1-(3-(Cyclopentyloxy-4-methoxyl)-phenyl)-cyclopent-1,2-ene-3-one.

In a further aspect the invention provides a compound of formula (I) for use as an active therapeutic substance.

In another aspect, the invention provides the use of a compound of formula (I) for the manufacture of a medicament for the treatment of cerebral vascular and neuronal degenerative disorders associated with learning, memory and cognitive dysfunctions including cerebral senility, multi-infarct dementia and senile dementia of the Alzheimer type and/or disorders resulting from an ischaemic event and/or peripheral vascular disease and/or proliferative skin diseases and/or reversible airways obstruction and/or asthma.

In another aspect, the invention provides the use of a compound of formula (I) or (I)' for the manufacture of a medicament for the inhibition of the production of tumor necrosis factor (TNF) and/or the prevention of TNF medicated disease states.

Each dosage unit for oral administration contains suitably from 1 mg to 100 mg/Kg, and preferably from 10 mg to 30 mg, and each dosage unit for parenteral administration contains suitably from 0.01 mg to 100 mg, of a compound of formula (I) or a pharmaceutically acceptable salt thereof calculated as the free base. Each dosage unit for intranasal administration contains suitably 1–400 $\mu$g and preferably 10 to 200 $\mu$g per person.

The daily dosage regimen for oral administration is suitably about 0.01 mg/Kg to 40 mg/Kg, of a compound formula (I) or a pharmaceutically acceptable salt thereof calculated as the free base. The daily dosage regimen for parenteral administration is suitably about 0.001 mg/Kg to 40 mg/Kg, for example about 0.001 mg/Kg to 40 mg/Kg, of a compound of the formula (I) or a pharmaceutically acceptable salt thereof calculated as the free base. The daily dosage regimen for intranasal administration and oral inhalation is suitably about 10 to about 1200 $\mu$g/person. The acitve ingredient may be administered from 1 to 6 times a day, sufficient to exhibit antiinflammatory activity.

The dosages and dosage regimen for compounds of formula (I)' are as described above.

The compounds of this invention are administered in an amount sufficient to inhibit TNF production such that normal or subnormal levels are achieved which are sufficient to ameliorate or prevent the disease state.

When used herein the term 'pharmaceutically acceptable' encompasses materials suitable for both human and veterinary use.

The following examples illustrate the invention. The following preparations illustrate the preparation of intermediates to the compounds of formula (I).

EXAMPLE 1

1-(3,4-Dimethoxyphenyl)-cyclopent-1,2-ene-3-one 5 g (0,023 mmol) 4-Bromo-veratole (commercially available) was dissolved in 250 ml n-hexane and treated with 15 ml butyl lithium (15% solution in n-hexane, 0,035 mol) at room temperature under nitrogen. After stirring for 2 hours 2,4 g (0,023mol) 1-ethoxycyclopent-1,2-ene-3-one in 20ml dry tetrahydrofuran was added and stirred at room temperature for 3 hours.

Then, the mixture was poured into ice-water, the organic layer separated and washed (3×) with water, dried over anhydrous sodium sulphate ($Na_2SO_4$) and evaporated to dryness. The residue was dissolved in a small portion of methylene chloride (10 ml). About 10 ml of diethylether was then added and the product precipitated by addition of 10–15ml petrol ether (40/80), yield 0.9 g (18%), m.pt. 152° C.

| M. Wt.: 218,25 | M. Formula $C_{13}H_{14}O_3$ | |
|---|---|---|
| NMR ($CDCl_3$) (ppm) | | |
| 2.45–2.7 | m | 2H |
| 2.9–3.15 | m | 2H |
| 3.93 | s | 6H |
| 6.47 | t | 1H |
| 6.8–7.4 | m | 3H |

EXAMPLE 2

1-(3-(Cyclopentyloxy-4-methoxy)-phenyl)-cyclopent-1,2-ene-3-one

The title compound was made according to Example 1, by using the following intermediates:

1 g (0,0037 mol) 4-bromo-2-cyclopentyloxy-1-methoxy-benzene; 3,2 ml (0,0074 mol) BuLl in n-hexane (solution); and 0.47 g (0.5 ml, 0.0037 mol) 1-ethoxycyclopent-1,2-ene-3-one.

The crude product was purified by thick-layer chromatography, using a mixture of chloroform-methanol (95:5) as eluent, yield 0.08g (9%), m.pt. 51° C.

| M. Wt.: 272,34 | M. Formula: $C_{17}H_{20}O_3$ | |
|---|---|---|
| NMR ($CDCl_3$) (ppm): | | |
| 1.3–2.3 | m | 12H |
| 2.45–2.7 | m | 2H |
| 2.9–3.15 | m | 2H |
| 3.9 | s | 3H |
| 6.45 | t | 1H |
| 6.8–7.4 | m | 3H |

EXAMPLE 3

1-(3-Cyclopentyloxy-4-methyoxyphenyl-cyclohex-1,2-ene-3-one

The title compound has been made according to Example 2 by using the following intermediates: 2.7 g (0.01mol) 4-bromo-2-cyclopentoxy-1-methoxybenzene; 7 ml (0.015 mmol) BuLl in n-hexane; and 1.4 g (0.01 mmol) of 1-ethoxy-1,2-cyclohexene-3-one in 30 ml n-hexane. The reaction was carried out under an argon-atmosphere, yield 1.1 g (38%) m.pt. 85° C.

| M. Wt.: 286.37, | M. Formula $C_{18}H_{22}O_3$. | |
|---|---|---|
| NMR ($CDCl_3$) (ppm): | | |
| 1.65–2.9 | m | 14H |
| 3.88 | s | 3H |
| 4.6–4.95 | m | 1H |
| 6.38 | m | 1H |
| 6.75–7.2 | m | 3H |

EXAMPLE 4

1-(3,4-Dimethoxyphenyl)-cyclohex-1,2-ene-3-one

The title compound was made according to Example 3. However the reaction time for this reaction was two days (instead of 2 hrs.) at room temperature. The crude compound was further purified by using medium-pressure chromotography (silica gel 60 A, 5 atmosphere, 25ml/min. $CHCl_3$).

The following intermediates were used:
45 g (0.21mol) 4-bromo-veratrole;
135 ml BuLi (15%ig in n-hexane); and
25 ml (0.21mol) 1-ethoxycyclohex-1,2-ene-3-one.
Yield: 5.2 g (10%), m.pt. 124° C.

| Yield: 5.2 g (10%), m. pt. 124° C. | | |
|---|---|---|
| M. Wt.: 232.28 | M. Formula: $C_{14}H_{16}O_3$ | |
| NMR ($CDCl_3$) (ppm) | | |
| 2.0–2.35 | m | 2H |
| 2.35–2.6 | m | 2H |
| 2.6–2.9 | m | 2H |
| 3.91 | s | 6H |
| 6.4 | s | 1H |
| 6.8–7.3 | m | 3H |

EXAMPLE 5

1-Methoxy-2-cyclopentyloxy-4-cyclohexyl-benzene 0.4 g (0.0014 mol) of the compound of Example 3 was dissolved in 50 ml absolute ethanol, 0.04 g Pd-C catalyst (palladium on charcoal) was added under argon-atmosphere and the mixture was hydrogenated using hydrogen (3 bar) at room-temperature for 6 hours. The catalyst was then filtered off and the solvent removed in vacuo. The crude residue was purified, using thick-layer chromatography (silica gel) with chloroform to give the title product as an oil.

| M. Formula: $C_{18}H_{26}O_2$. | M. Wt.: 274.40 | |
|---|---|---|
| NMR ($CDCl_3$) (ppm): | | |
| 1.1–2.8 | m | 19H |
| 3.81 | s | 3H |
| 4.6–4.9 | m | 1H |
| 6.6–6.95 | m | 3H |

EXAMPLE 6

1,2-Dimethoxy-4-cyclohexyl-benzene

The compound has been made according to Example 5 using the following intermediates: 2 g (0.0086 mol) of Example 4, was hydrogenated in 50 ml absolute ethanol using 2 g Pd-charcoal catalyst. The hydrogenation was effected at 2.2 atmosphere pressure for 8 hours, yield: 0.06 g (1.1%). The title product was obtained as an oil.

| M. Wt.: 220.31. | M. Formula: $C_{14}H_{20}O_2$ | |
|---|---|---|
| NMR ($CDCl_3$) (ppm) | | |
| 1.0–2.7 | m | 11H |
| 3.85 and 3.87 | 2xs | 6H |
| 6.65–7.95 | m | 3H |

EXAMPLE 7

3-(3-Cyclopentyloxy-4-methoxyphenyl)cyclopent-2-en-1-one (E7)

To a solution of 4-bromo-2-cyclopentyloxy-1-methoxybenzene (preparation 4) (9.50 g, 35.0 mmol) in tetrahydrofuran (70 ml) at −78° C. under an argon atmosphere was added dropwise n-butyllithium (15 ml of 2.5M solution, 37.5 mmol). The resulting mixture was stirred at −78° C. for 1.25 hr and added dropwise to a cooled solution (0° C.) of 3-isopropoxy-2-cyclopentenone (4.95 g, 35.3 mmol) in tetrahydrofuran (20 ml). Upon completion of the addition, the reaction mixture was allowed to warm to room temperature and was stirred for 1.5 hr. Hydrochloric acid (70 ml of 0.6N solution) was added to the reaction mixture and stirring was continued for 2.5 hr. The reaction mixture was poured into water and extracted with methylene chloride (four times). The combined organic extracts were dried (magnesium sulfate), the solvent was removed in vacuo and the residue was purified by flash chromatography, eluting with 1:4:5 methylene chloride/ether/hexanes. Recrystallization from methylene chloride/ether/hexanes provided needles (5.5 g, 63%): m.p. 136°–137° C. Analysis:

Analysis: Calc. for $C_{17}H_{20}O_3$: C74.97, H7.40; found: C74.96, H7.32.

EXAMPLES 8 and 9

3-(3-Cyclopentyloxy-4-methoxyphenyl)cyclopentan-1-one (E8) and
cis-3-Cyclopentyloxy-4-methoxyphenyl)cyclopentan-1-ol (E9)

To a solution of 3-(3-Cyclopentyloxy-4-methoxyphenyl) cyclopent-2-en-1-one (2.5 g, 9.18 mmol) in methanol (200 ml) containing 4 drops of 50% aqueous potassium hydroxide was added 10% palladium on activated carbon (2.2 g) and the resulting mixture was hydrogenated at 60 psi for 5 hr. The mixture was filtered through a pad of Celite and concentrated under reduced pressure. The residue was purified by flash chromatography, eluting with 40% ether/hexanes to provide the ketone (E8) (1.75 g, 70%): m.p. 79.5°–80° C.

Analysis: Calc. for $C_{17}H_{22}O_3$: C74.42, H8.08; found: C74.61, H8.07.

Also isolated was the corresponding alcohol (E9) with predominant cis relative configuration (0.35 g, 14%).

Analysis: Calc. for $C_{17}H_{24}O_3$: C73.88, H8.75; found: C73.37, H8.48.

EXAMPLE 10

3-(3-Cyclopentyloxy-4-methoxyphenyl)cyclopent-2-en-1-ol (E10)

To a solution 3-(3-Cyclopentyloxy-4-methoxyphenyl)cyclopent-2-en-1-one (275 mg, 1.01 mmol) (E7) in benzene (5 ml) at 0° C. under an argon atmosphere was added a toluene solution of diisobutylaluminum hydride (1M, 1.5 ml, 1.5 mmol) and the resulting mixture was stirred at 0° C. for 1 hr. The mixture was treated with methanol (5 ml), poured into ether (100 ml), filtered and concentrated under reduced pressure. The crude product was combined with the product to a similar reaction conducted on 55 mg of ketone and was purified by flash chromatography, eluting with 5:3.5:1 hexanes/ether/methylene chloride to provide a solid. Recrystallization from hexanes/ether provided the title compound (92 mg, 27.7%): m.p. 105°–107° C.; an additional 150 mg was recovered from the mother liquor.

Analysis: Calc. for $C_{17}H_{22}O_3$: C74.42, H8.08; found: C74.42, H8.10.

EXAMPLE 11

3-(3-Cyclopentyloxy-4-methoxyphenyl)-1-methoxycyclopent-2-ene (E11)

3-(3-Cyclopentyloxy-4-methoxyphenyl)-cyclopent-2-en-1-ol (150 mg, 0.55 mmol) (E10) was added to a suspension of powdered potassium hydroxide (89%, 138 mg, 2.2 mmol) under an argon atmosphere and then iodomethane (35μl, 0.56 mmol) was added. The resulting mixture was stirred at room temperature for 3 hr, poured into water and extracted with ether. The ether extracts were washed three times with water, dried (sodium sulfate) and concentrated under reduced pressure. Purification by flash chromatography, eluting with 2:1 hexanes/ether, provided the title compound as an oil (120 mg, 76%).

Analysis: Calc. for $C_{18}H_{24}O_3$: C74.97, H8.39; found: C75.59, H8.13.

EXAMPLE 12 trans-3-(3-Cyclopentyloxy-4-methoxyphenyl)-cyclopentan-1-ol (E12)

3-(3-Cyclopentyloxy-4-methoxyphenyl) -cyclopentan-1-ol, (predominantly cis, 160 mg, 0.58mmol) (E9) in freshly distilled tetrahydrofuran (5 ml) was stirred vigorously with diethylazodicarboxylate (96μl 0.58 mmol), triphenylphosphine (152 mg, 0.58mmol) and glacial acetic acid (35μl, 0.61 mmol) under an argon atmosphere at room temperature for 24 hr. The liquids were removed under reduced pressure, with purification by flash chromatography, eluting with 2:1 hexanes/ether, providing and trans acetate as an oil (133 mg, 72%). This oil (133 mg, 0.42 mmol) in methanol (2 ml) was treated with potassium hydroxide (89%, 52 mg 0.82 mmol) in water (0.3 ml) for 1 hr. The mixture was partitioned between ether and water, the ether was dried (potassium carbonate) and the solvent was removed in vacuo. Purification by flash chromatography, eluting with 1:1 hexanes/ether, provided the title compound as an oil (89 mg, 55.6%).

EXAMPLE 13 cis-3-(3-Cyclopentyloxy-4-methoxyphenyl-1-methoxycyclopentane (E13)

3-(3-Cyclopentyloxy-4-methoxyphenyl)-cyclopentan-1-ol (predominantly cis, 130 mg, 0.47 mmol) (E9) in methylene chloride (5 ml) was stirred vigorously with aqueous sodium hydroxide (50%, 0.2 ml), tetrabutylammonium bromide (3 mg) and dimethylsulfate (0.1 ml, 1.05 mmol) under an argon atmosphere. The resulting mixture was stirred at room temperature for 24 hr, whereupon additional aqueous sodium hydroxide (0.2 ml), tetrabutylammonium bromide (3 mg) and dimethylsulfate (0.1 ml) were added. After an additional 72 hr, the mixture was poured into water and extracted with methylene chloride. The extracts were dried (sodium sulfate) and concentrated under reduced pressure. Purification by flash chromatography, eluting with 1.5:1 ether/hexanes, provided the title compound as an oil.

Analysis: Calc. for $C_{18}H_{26}O_3$: $\frac{1}{8}H_2O$: C73.87, H9.04; found: C73.51, H8.67.

Preparation 1

1-Methoxy-2-hydroxy-4-bromo-benzene

The compound is described in the literature: Paty, Quelet, Bl.[5] 11 (1944) 505,509

Preparation 2

1-Methoxy-2-cyclopentyloxy-4-bromo-benzene 20 g (0.1 mol) 1-Methoxy-2-hydroxy-4-bromo-benzene (Preparation 1) was dissolved in 40 ml ethanol. Then 21 g (0.14 mol) cyclopentylbromide and a solution of 5.5 g NaOH in 6.6 ml water was added and the mixture refluxed for 13 hours. Thereafter, the solvent was removed in vacuo and the residue taken up with methylene chloride and washed (4×) with 1N NaOH. After drying over $Na_2SO_4$, the organic solvent was removed in vacuo to give the title compound as an oily product, yield: 182 g (67%).

| NMR (CDCl$_3$) (ppm): | | |
|---|---|---|
| 1.4–2.15 | m | 8H |
| 3.78– | s | 3H |
| 4.55–4.9 | m | 1H |
| 6.55–7.1 | m | 3H |

Preparation 3

5-Bromo-2-methoxyphenol. To a solution of 5-bromo-2 methoxybenzaldehyde (32.25 g, 0.15 mol) in methanol (300 ml) was added hydrogen peroxide (38 ml of 30% aqueous solution, 0.34 mol) and concentrated sulfuric acid (7 ml, 0.13 mol). The resulting solution was heated at 70° C. for 3 hr. and allowed to cool to room temperature. Stirring was continued for 60 hr. and the reaction mixture was concentrated under reduce pressure. The residue was partitioned between ether and water and the organic extract was washed with slightly acidic water (three times) and dried (magnesium sulfate). The solvent was removed in vacuo to provide an orange solid (30.6 g) which was used without further purification.

Preparation 4

4-Bromo-2-cyclopentyloxy-1-methoxybenzene. To a solution 5-Bromo-2-methoxyphenol (30.6 g, 0.15 mmol) (preparation 3) in N, N-dimethylformamide (130 ml) under an argon atmosphere was added potassium carbonate (23.0 g, 0 . 17tool) and cyclopentyl bromide (18 ml, 0.18 mol). The resulting mixture was heated at 90° C. for 20 hr., at which time additional potassium carbonate (5.6 g, 0.04 mol) and cyclopentyl bromide (3 ml, 0.03 mmol) were added. Heating was resumed for 8 hr and additional potassium carbonate (5.6 g, 0.04 mol) and cyclopentyl bromide (3 ml, 0.03 mmol) were added. After heating at 90° C. for an additional 16 hr, the reaction mixture was allowed to cool and was concentrated under reduced pressure. The residue was partitioned between ether and water. The organic extract was washed with water (three times) and dried (magnesium sulfate). The solvate was removed in vacuo and the residue was purified by flash chromatography, eluting with 3% ether/hexanes to provide a pale yellow oil (29.8 g, 73%).

PHARMACOLOGICAL DATA a) Inhibition of Cyclic AMP Phosphodiesterase

Procedure

The procedure used was that described by Arch, J. R. S. and Newsholme, E. A. in Biochem. J. 158, 603, (1976):

Erythrocytes were obtained from Na-citrate (16 mM; 0.1 ml/ml blood) anticoagulated blood by repeated centrifugation with removal of the buff coat and washing with an isotonic buffer (composition in mM: NaCl 13.7, KCl 4, $CaCl_{2.2}$ $H_2O$ 1.8, $Na_2HPO_4.12$ $H_2O$ 0.8, $NaH_2PO_4$ 0.2, $MgSO_4.7$ $H_2O$ 0.7, Hepes 3.4; pH 7.4).

The phosphodiesterase was extracted by mixing the erythrocytes with 4 volumes of 7 mM phosphate buffer, pH7.4, followed by sonification ($3 \times 10$ sec; 100 W) and then centrifuging for 30 min at $4200 \times g$.

All supernatants were diluted in the extraction medium and assayed for phosphodiesterase activity within 6 hours of preparation, using the radiochemical procedure described in the above mentioned reference.

Results

| Example 1 No. | Ki [μM] c-AMP phosphodiesterase (erythrocytes) |
|---|---|
| 1 | 10.9 |
| 2 | 1.1 |
| 3 | 0.7 |
| 4 | 3.0 |
| 5 | 2.1 |
|   | 14.1 |

The biological activity of the compounds of formula I are further demonstrated by the following tests.

I Isolation of PDE Isozymes

Phosphodiesterase inhibitory activity and selectivity of compounds is determined using a battery of five distinct PDE isozymes. The characteristics of these PDEs appear in Table 1. The tissues used as sources of the different isozymes are as follows: 1) PDE Ia, canine trachealis; 2) PDE Ib, porcine aorta; 3) PDE Ic, guinea-pig heart; 4) PDE III, guinea-pig heart; and 5) PDE IV, human monocyte. PDEs Ia, Ib, Ic and III are partially purified using standard chromatographic techniques (Torphy and Cieslinski, Mol. Pharmacol. 37: 206–214, 1990). PDE IV is purified to kinetic homogeneity by the sequential use of anion-exchange followed by heparin-Sepharose chromatography (White et al., FASEB J. 4: A1987 1990).

TABLE 1

Characteristics of PDE isozymes.[a]

| Peak | Isozyme[b] | $K_m$ (mμM) cAMP | cGMP |
|---|---|---|---|
| Ia | cGMP-specific | 135 | 4 |
| Ib | $Ca^{2+}$/calmodulin-stimulated | 50 | 5 |
| Ic | $Ca^{2+}$/calmodulin-stimulated | 1 | 2 |
| III | cGMP-inhibited | 0.4 | 8 |
| IV | Ro 20-1724-inhibited | 4 | 38 |

[a]Data are from Torphy and Cieslinski, supra.
[b]Nomenclature is from Beavo, Adv. Second Messenger Phosphoprotein Res. 22: 1–38, 1988.

II PDE Assay

Phosphodiesterase activity is assayed as described in Torphy and Cieslinski, Mol. Pharmacol. 37: 206–214, 1990. The reaction is conducted in 0.1 ml of standard mixture containing (final concentrations): 50 mM Tris-HCl buffer (pH 7.5), 5 mM $MgCl_2$, 50 μM [$^{14}$C]-5'AMP (approximately 400 dpm/nmole) as a carrier and for determining recovery of product, 1 μM [$^{3}$H]-cAMP (approximately 2000 dpm/pmole), enzyme, and vehicle or various concentrations of test compounds. The reaction is initiated with either enzyme or substrate and conducted at 30° C. The reaction is terminated by placing reaction vessels in a 100° C. heating block for 1 min. To separate cyclic nucleotide substrates from 5'-nucleotide products, 0.5 ml of 0.1 M Hepes buffer (pH 8.5) containing 0.1 M NaCl is first added to each sample. The entire sample is then applied to a polyacrylamide-boronate gel column (0.5 g of Biorad Affi-gel 601* in a $0.7 \times 10$ cm Biorad* (*registered trade marks) econo-column) which has been equilibrated with the 0.1 M Hepes/ 0.1 M NaCl buffer (pH 8.5). The unreacted cyclic nucleotides are eluted with 8' ml of equilibration buffer.

The 5'-monophosphate products are eluted with 10 ml of 0.25 M acetic acid into a scintillation vial containing 10 ml of scintillation cocktail.

Recovery of [$^{3}$H]5'-AMP, as determined with the [$^{14}$C]5'AMP carrier, is 80–90%. All assays are conducted in the linear range of the reaction where less than 20% of the initial substrate is hydrolyzed.

Cyclic GMP hydrolysis is assayed using a protocol identical to the one described above, with [$^{3}$H]cGMP as the substrate. [$^{3}$H]cGMP is used as the substrate for PDEs Ia, Ib and Ic. [$^{3}$H]cAMP is used as the substrate for PDEs III and IV.

$IC_{50}$s for compounds of this invention range from 0.5 μM to 40 μM.

III cAMP Accumulation in U-937 cells

The ability of selected PDE IV inhibitors to increase cAMP accumulation in intact tissues is assessed using U-937 cells, a human monocyte cell line that has been shown to contain a large amount of PDE IV. Approximately $2 \times 10^6$ cells in a volume of 100 μl are incubated at 37° C. in a Krebs-Ringer buffer (pH 7.5) containing (mM): $CaCl_2$, 1; Hepes, 5; glucose, 1.1; NaCl, 118; KCl, 4.6; $NaHCO_3$, 24.9; $KH_2PO_4$, 1; BSA, 0.2 mg/ml. Cells are treated with various concentrations of test compounds (PDE inhibitors) for 1 rain before the addition of a threshold concentration of $PGE_2$ (0.1 µM). Four minutes after the addition of $PGE_2$, the reaction is stopped with 100 µl of 17.5% $HClO_4$ and then neutralized with 150 µl of 1M $K_2CO_3$. 550 µl of sodium acetate buffer (pH 6.8) is then added to the neutralized solution. Permeabilized cells and cell debris are removed from the soluble fraction via centrifugation (1800 ×g for 5 min). The supernatant is then assayed for cAMP via radioimmunoassay using commercially available kits (Dupont/New England Nuclear, Cambridge, Me.). The effects of test compounds are compared to those of racemic rolipram, which is used as a standard in all experiments. Data are expressed as both an $EC_{50}$ for increases in cAMP accumulation as a percentage of the maximum response to rolipram produced by 10 µM of the test compounds. $EC_{50}$s for compounds of this invention range from 0.5 µM to >10µM.

Inhibitory Effect of compounds of Formula (1) on in vitro TNF production of Human Monocytes Section I: Assay set-up The effects of compounds of Formula (I) and (I)' on the in vitro production of TNF by human monocytes was examined using the following protocol.

Human peripheral blood monocytes were isolated and purified from either blood bank buffy coats or plateletpheresis residues, according to the procedure of Colotta, R. et al., *J Immunol.*, 132(2):936(1984). The monocytes were plated at a density of $1 \times 10^6$ cells/ml medium/well in 24-well multidishes. The cells were allowed to adhere for 1 hour after which time the supernatant was aspirated and 1 ml fresh medium (RPMI-1640 (Whitaker Biomedical Products, Whitaker, Calif.)) containing 1% fetal calf serum and penicillin and streptomycin at 10 units/ml was added. The cells were incubated for 45 minutes in the presence or absence of test compounds at 1nM-10uM dose ranges (compounds were solubilized in Dimethyl-sulfoxide/Ethanol such that the final solvent concentration in the culture medium was 0.5% Dimethyl sulfoxide/0.5% Ethanol). Bacterial lipopolysaccharide (*E. coli* 055:B5 [LPS]from Sigma Chemicals Co.) was then added at 100 ng/ml in 10 ml Phosphate Buffered Saline (PBS) and cultures incubated for 16-18 hours at 37° C. in a 5% $CO_2$ incubator. At the end of the incubation period, culture supernatants were removed from the cells, centrifuges at 3000 revolutions per minute (rpm) to remove cell debris and 0.05 ml of the supernatant assayed for TNF activity using the radioimmunoassay described below.

Section II: Radioimmunoassay procedure for TNF activity

The assay buffer consisted of 0.01M $NaPO_4$, 0.15M NaCl, 0.025M EDTA and 0.1% sodium azide at pH 7.4 Human recombinant TNF (rhTNF) obtained using the procedure of Chen et al., *Nature*, 330:581-583 (1987) was iodinated by a modified Chloramine-T method described in Section III below. To samples (50 µl culture supernatants) or rhTNF standards, a 1/9000 dilution of polyclonal rabbit anti-rhTNF (Genzyme, Boston, Me.) and 8000 cpm of $^{125}I$-TNF was added in a final volume of 400 µl buffer and incubated overnight (18 hours) at 4° C. Normal rabbit serum and goat anti-rabbit IgG (Calbiochem) were titered against each other for maximum precipitation of the anti-rhTNF. The appropriate dilutions of carrier normal rabbit serum (1/200), goat anti-rabbit IgG (¼) and 25 Units heparin (Calbiochem) were allowed to precipitate and 200 µl of this complex was added per assay tube and incubated overnight at 4° C. Tubes were centrifuged for 30 minutes at 2000 rpm, supernatants were carefully aspirated, and radioactivity associated with the pellets measured in a Beckman Gamma 5500 counter. The logit-log linear transformation curve was used for the calculations. The concentrations of TNF in the samples was read of a standard curve of rhTNF that was linear in the 157 to 20,000 pg/ml range.

Section III: Radioiodination of rhTNF

Iodination of rhTNF was performed using a modified chloramine-T method of Frolik et al., *J. Biol. Chem.* 259:10995-11000 (1984). Briefly, 5 mg of rhTNF in 5 ml of 20MM Tris ph 7.5, was diluted with 15 ml of 0.5 M $KPO_4$ and 10 ml of carrier free 125I (100 mCi/ml;ICN). To initiate the reaction, a 5 ml aliquot of a 100 mg/ml (aqueous) chloramine-T solution was added. After 2 minutes at room temperature, an additional 5 ml aliquot was added followed 1.5 minutes later by a final 5 ml addition of chloramine-T. The reaction was stopped 1 minute later by sequential addition of 20 ml of 50 mM Sodium Metabisulfite, 100 ml of 120 mM Potassium Iodide and 200 ml of 1.2 mg/ml Urea. The contents were mixed and the reaction mixture was passed over a pre-packed Sephadex G-25 column (PD 10 Pharmacia), equilibrated and eluted with Phosphate Buffered Saline pH 7.4 containing 0.25% gelatin. The peak radioactivity containing fractions were pooled and stored at −20° C. Specific activity of $^{125}I$-TNF was 80-100 mCi/mg protein. Biological activity of iodinated TNF was measured by the L929 cytotoxicity assay of Neale, M. L. et al., *Eur. J. Can. Clin. Oncol.*, 25(1):133-137 (1989) and was found to be 80% that of unlabeled TNF.

Section IV:Mesaurement of TNF-ELISA:

Levels of TNF were also measured using a modification of the basic sandwich ELISA assay method described in Winston et al., *Current Protocols in Molecular Biology*. Page 11.2.1, Ausubel et al., Ed. (1987) John Wiley and Sons, New York, USA. The ELISA employed a murine monoclonal anti-human TNF antibody, described below, as the capture antibody and a polyclonal rabbit anti-human TNF, described below, as the second antibody. For detection, peroxidase-conjugated goat anti-rabbit antibody (Boehringer Mannheim, Indianopolis, Ind., USA, Catalog#605222) was added followed by a substrate for peroxidase (1 mg/ml orthophenylenediamine with 0.1% urea peroxide). TNF levels in samples were calculated from a standard curve generated with recombinant human TNF produced in *E. Coli* (obtained from SmithKline Beecham Pharmaceuticals, King of Prussisa, Pa., USA).

Section V: Production of anit-human TNF antibodies

Monoclonal antibodies of human TNF were prepared from spleens of BALB/c mice immunized with recombinant human TNF using a modification of the method of Kohler and Millstein, *Nature* 256:495 (1975), the entire disclosure of which is hereby incorporated by reference. Polyclonal rabbit anti-human TNF antibodies were prepared by repeated immunization of New Zealand (NZW) rabbits with recombinant human TNF emulsified in complete Freund's adjuvant (DIFCO, IL., USA). Endotoxin Endotoxin Shock in D-gal-Senstized Mice The protocol used to test the compound of the method of the subject invention was essentially as has been described in Galanos et al., *Proc. Natl. Acad. Sci. USA*, 76:5939-43 (1979) whose disclosure is herein incorporated by reference. Briefly, D-gal (D (+) Galactosidase) sensitizes various strains of mice to the lethal effects of endotoxin. The administration of D-gal (300–500 mg/kg) intra-venously (i.v.) sensitizes the mice to doses of lipopolysaccharide (LPS) as low as 0.1 μg. Briefly, male C57BL/6 mice, obtained from Charles River Laboratories (Stone Ridge, N.Y., USA) of 6–12 weeks of age were injected i.v. with 0.1 μg of LPS from *Salmonella typhosa* (Difco Laboratories, Detroit, Mich., USA) admixed with D(+)-gal (Sigma; 500 mg/kg) in 0.20–0.25 ml pyrogen-free saline. Compounds to be tested were administered at various times prior to or following the i.v. injection of LPS/D-gal. In this model, the control animals usually die 5–6 hr. following the injection of LPS, although on occasion deaths are seen between 24 and 48 hr.

Measurement of TNF Activity

Plasma levels of TNF were measured using a modification of the basic sandwich ELISA method described in Winston et al., *Current protocols in Molecular Biology*, Pg. 11.2.1, Ausubel et al., Ed. (1987) John Wiley and Sons, New York, USA. The Elisa employed a hampster monoclonal anti-mouse TNF (Genzyme, Boston, Me., USA) as the capture antibody and a polyclonal rabbit anti-murine TNF (Genzyme, Boston, Me., USA) as the detecting antibody. TNF levels in mouse samples were calculated from a standard curve generated with recombinant murine TNF (Genzyme, Boston, Me., USA) TNF levels determined by ELISA correlated with levels detected by the L929 bioassay of Ruff et. al., *J. Immunol*, 125:1671–1677 (1980), with 1 Unit of activity in the bioassay corresponding to 70 picograms (pg) of TNF in the ELISA. The ELISA detected levels of TNF down to 25 pg/ml.

We claim:

1. A compound of formula (I) or a pharmaceutically acceptable salt thereof:

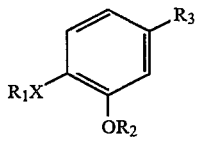

$R_1$ is —$CH_3$ or —$CH_2CH_3$ unsubstituted or substituted by 1 to 3 fluorine;
X is O or $S(O)_s$ where s=0 to 2;
$R_2$ is $C_4$- cyclic alkyl, optionally substituted by one to three methyl groups or one ethyl group; —$CH_2$-cyclopentyl, —$CH_2$-cyclopropyl, 3-tetrahydrofuranyl, $C_{1-7}$ alkyl, $CH_3$ or $CH_2CH_3$ substituted by one to three fluorines;
—$(CH_2)_nCOO(CH_2)_gCH_3$, or $(CH_2)_nO(CH_2)_gCH_3$, wherein n is 2 to 4 and g is 0 to 2;

$R_3$ represents a moiety of formula (a):

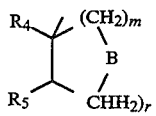

wherein $R_4$ and $R_5$ each represent hydrogen or $R_4$ and $R_5$ together represent a bond; B represents >C=O, >C=S or >CH—$R_6$ wherein $R_6$ represents H, OH, $C_{1-6}$ alkoxy or $C_{1-6}$ thioalkoxy; and m and r each independently represents zero or an integer in the range of 1 to 4 wherein m+r represents an integer in the range of from 2 to 4; with the proviso that when $R_1$ is methyl, X is oxygen, $R_2$ is [methyl or]cyclopentyl, $R_3$ does not represent cyclopent-1,2-ene-3-one.

2. A compound according to claim 1 in which $R_1$ represents methyl and X represents oxygen.

3. A compound according to claim 1 in which $R_2$ represents unsubstituted $C_{4-6}$ cycloalkyl.

4. A compound according to claim 1 in which $R_2$ represents cyclopentyl or methyl.

5. A compound according to claim 1 in which $R_3$ is selected from the following structures;

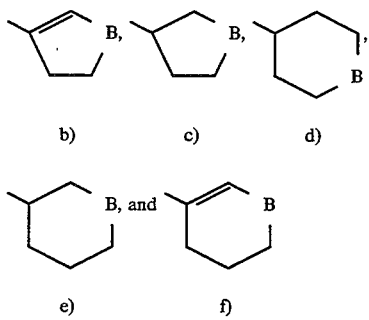

in which B is C=O, $CH_2$, $CH_2OH$ or $CH_2OCH_3$.

6. A compound according to claim 5 in which $R_3$ is of formula b) or c) and B is carbonyl, $CH_2OH$ or $CH_2OCH_3$.

7. A compound selected from the group consisting of:
1-(3-(cyclopentyloxy-4-dimethoxy)-phenyl)-cyclohex-1,2-ene-3-one,
1-methoxy-2-cyclopentyloxy-4-cyclohexylbenzene, and
1,2-methoxy-4-cyclohexyl-benzene.

8. A compound selected from the group consisting of:
3-(3-cyclopentyloxy-4-methoxyphenyl)cyclopent-2-en-1-one,
3-(3-cyclopentyloxy-4-methoxyphenyl)cyclopentan-1-one,
cis-3- (3-cyclopentyloxy-4-methoxyphenyl) cyclopentan-1-ol,
3-(3-cyclopentyloxy-4-methoxyphenyl)cyclopent-2-en-1-ol,
3-(3-cyclopentyloxy-4-methoxyphenyl)-1-methoxycyclopent-2-ene,
trans-3-(3-cyclopentyloxy-4-methoxyphenyl)-cyclopentan-1-ol, and
cis-3-(3-cyclopentyloxy-4-methoxyphenyl)-1-methoxycyclopentane.

* * * * *